(12) United States Patent
    Burkholz et al.

(10) Patent No.: US 11,819,639 B2
(45) Date of Patent: Nov. 21, 2023

(54) SYSTEMS AND METHODS FOR CATHETER INSERTION AND BLOOD FLASHBACK

(71) Applicant: Becton, Dickinson and Company, Franklin Lakes, NJ (US)

(72) Inventors: Jonathan Karl Burkholz, Salt Lake City, UT (US); Bin Wang, Sandy, UT (US)

(73) Assignee: Becton, Dickinson and Company, Franklin Lakes, NJ (US)

(*) Notice: Subject to any disclaimer, the term of this patent is extended or adjusted under 35 U.S.C. 154(b) by 1104 days.

(21) Appl. No.: 16/518,724

(22) Filed: Jul. 22, 2019

(65) Prior Publication Data
    US 2020/0046948 A1  Feb. 13, 2020

Related U.S. Application Data

(60) Provisional application No. 62/715,662, filed on Aug. 7, 2018.

(51) Int. Cl.
    *A61M 25/06*  (2006.01)
    *A61M 39/10*  (2006.01)
    (Continued)

(52) U.S. Cl.
    CPC ... *A61M 25/0693* (2013.01); *A61B 5/150992* (2013.01); *A61M 5/158* (2013.01);
    (Continued)

(58) Field of Classification Search
    CPC ............. A61M 39/105; A61M 39/28; A61M 2039/1077; A61M 2039/205;
    (Continued)

(56) References Cited

U.S. PATENT DOCUMENTS 4,193,399 A * 3/1980 Robinson .......... A61M 25/0693
                                              96/219
4,311,137 A * 1/1982 Gerard ............. A61M 25/0606
                                              604/122
(Continued)

FOREIGN PATENT DOCUMENTS

CN    101563121    10/2009
CN    106620941     5/2017
(Continued)

*Primary Examiner* — Katherine H Schwiker
*Assistant Examiner* — Adam J. Cermak
(74) *Attorney, Agent, or Firm* — Kirton McConkie; Whitney Blair; Kevin Stinger

(57) ABSTRACT

A method may include priming a catheter system. The catheter system may include a catheter adapter, a catheter, and an extension tube. The catheter system may also include a Y-adapter, which may include first and second arms. A distal end of the Y-adapter may be coupled to the extension tube. The catheter system may further include a vent cap, which may be coupled to the second arm. Priming the catheter system may include attaching an IV line to the first arm and delivering saline through the IV line to the catheter system such that the saline exits a distal tip of the catheter and clamping the IV line via a roller clamp on the IV line. The method may also include actuating the vent cap after priming the catheter system. The method may further include inserting the catheter into a vein of a patient after actuating the vent cap.

4 Claims, 12 Drawing Sheets

(51) Int. Cl.
    *A61M 39/20*      (2006.01)
    *A61M 39/28*      (2006.01)
    *A61B 5/15*       (2006.01)
    *A61M 5/158*      (2006.01)
    *A61M 5/14*       (2006.01)

(52) U.S. Cl.
    CPC ........ *A61M 25/065* (2013.01); *A61M 39/105* (2013.01); *A61M 39/20* (2013.01); *A61M 39/28* (2013.01); *A61M 2005/1402* (2013.01); *A61M 2039/1077* (2013.01); *A61M 2039/205* (2013.01)

(58) Field of Classification Search
    CPC ...... A61M 25/0693; A61M 2005/1402; A61M 25/0606; A61B 5/150992
    See application file for complete search history.

(56) References Cited

U.S. PATENT DOCUMENTS

| | | | |
|---|---|---|---|
| 6,719,726 | B2 | 1/2004 | Meng et al. |
| 8,066,670 | B2 | 11/2011 | Cluff et al. |
| 11,389,584 | B2 * | 7/2022 | Truong ............... A61M 5/1452 |
| 11,413,220 | B2 * | 8/2022 | Davis .................. A61J 15/0076 |
| 2008/0287906 | A1 | 11/2008 | Burkholz et al. |
| 2011/0054403 | A1 * | 3/2011 | Tanabe ................. A61M 5/158 |
| | | | 604/164.01 |
| 2017/0239443 | A1 | 8/2017 | Abitabilo et al. |
| 2022/0369971 | A1 * | 11/2022 | Bullington ....... A61B 5/150221 |

FOREIGN PATENT DOCUMENTS

| | | |
|---|---|---|
| CN | 211188776 | 8/2020 |
| WO | 2017/074676 | 5/2017 |
| WO | 2018/009653 | 1/2018 |

\* cited by examiner

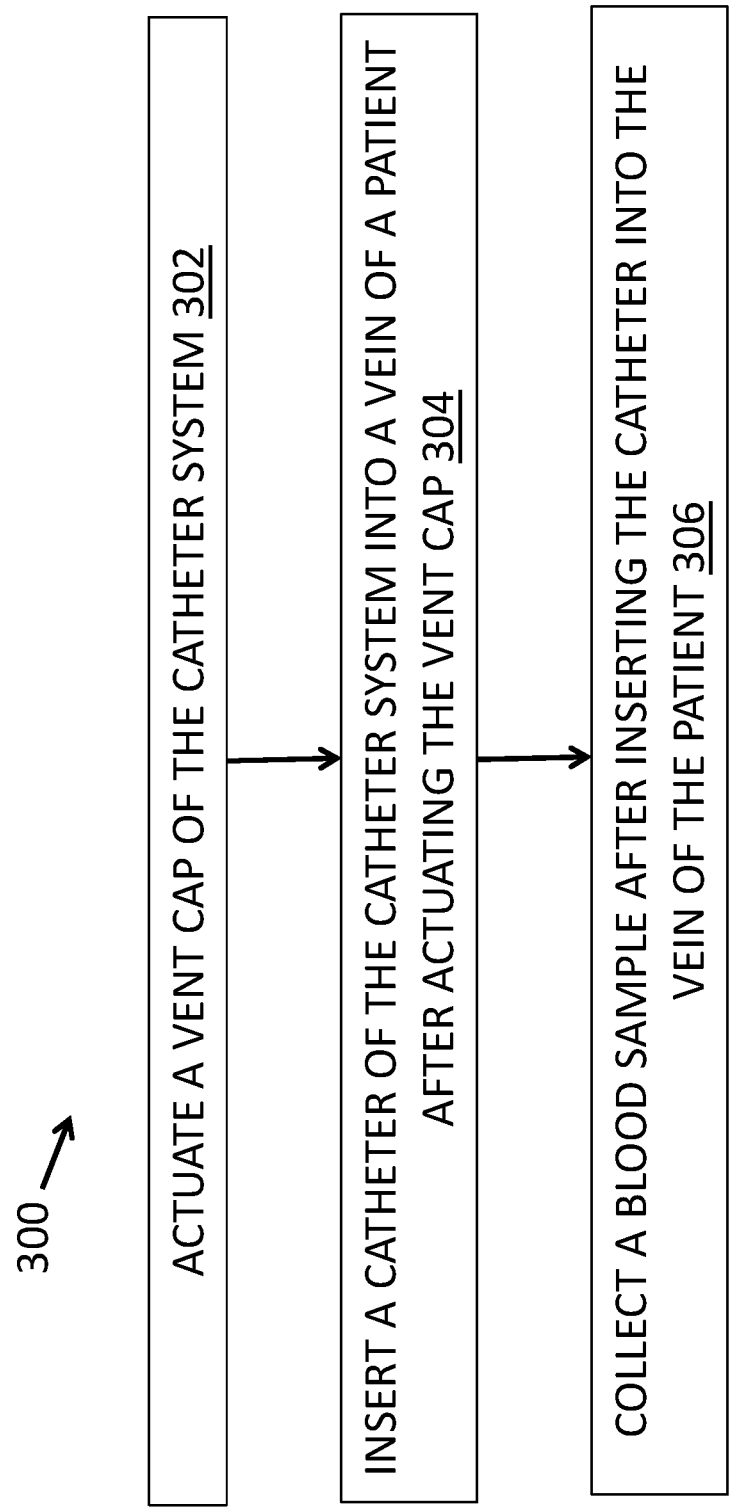

SYSTEMS AND METHODS FOR CATHETER INSERTION AND BLOOD FLASHBACK

RELATED APPLICATIONS

This application claims the benefit of U.S. Application No. 62/715,662, filed Aug. 7, 2018, and entitled SYSTEMS AND METHODS FOR CATHETER INSERTION AND BLOOD FLASHBACK, which is incorporated herein in its entirety.

BACKGROUND

Infusion therapy, a common healthcare procedure, may be facilitated by a vascular access device. Hospitalized, home care, and other patients receive fluids, pharmaceuticals, and blood products via a vascular access device inserted into the vascular system. Blood withdrawal is another common healthcare procedure that may be facilitated by a vascular access device.

A vascular access device may access a peripheral or central vasculature of a patient. A vascular access device may be indwelling for short term (days), moderate term (weeks), or long term (months to years). A vascular access device may be used for continuous infusion therapy or for intermittent therapy.

A common type vascular access device is an over-the-needle peripheral intravenous catheter (PIVC). As its name implies, the "over-the-needle" PIVC may be mounted over an introducer needle having a sharp distal tip. The sharp distal tip may be used to pierce skin and the vasculature of the patient. Insertion of the PIVC into the vasculature may follow the piercing of the vasculature by the needle. The needle and the PIVC are generally inserted at a shallow angle through the skin into the vasculature of the patient with a bevel of the needle facing away from the skin of the patient.

In order to verify proper placement of the introducer needle and/or the PIVC in the blood vessel, a user generally confirms that there is "flashback" of blood in an annular space between the catheter and the needle, or in a flashback chamber of the catheter assembly. Once flashback has been confirmed, the user may temporarily occlude flow in the vasculature and remove the needle, leaving the catheter in place for future blood withdrawal or fluid infusion.

In some markets, priming of the PIVC is common practice prior to insertion of the PIVC into the vasculature of the patient. In order to prime the PIVC, the user may fill the PIVC with saline or another priming fluid to reduce or eliminate any air pockets disposed within the PIVC. The saline may also fill all or a portion of a needle lumen. For example, the saline may fill a portion of the needle lumen proximate a notch in the needle, as well as distal to the notch, all the way to the distal tip of the introducer needle.

The subject matter claimed herein is not limited to embodiments that solve any disadvantages or that operate only in environments such as those described above. Rather, this background is only provided to illustrate one example technology area where some implementations described herein may be practiced.

SUMMARY

The present disclosure relates generally to systems and methods for catheter insertion and blood flashback. In some embodiments, a method of placing a catheter into a vein of a patient may include priming a catheter system. In some embodiments, the catheter system may include a catheter adapter, a catheter extending distally from the catheter adapter, and an extension tube extending from the catheter adapter. In some embodiments, the catheter adapter may include a side port and/or the extension tube may extend from the side port. In some embodiments, the catheter adapter may include a proximal end and a distal end. In some embodiments, the extension tube may extend from the proximal end of the catheter adapter.

In some embodiments, the catheter system may also include a Y-adapter, which may include a distal end, a first arm, and a second arm. In some embodiments, the distal end of the Y-adapter may be coupled to the extension tube. In some embodiments, the catheter system may further include a vent cap, which may be coupled to the second arm. In some embodiments, the first arm may correspond to either a central arm or a side arm of the Y-adapter. In some embodiments, the second arm may correspond to either the central arm or the side arm of the Y-adapter. In some embodiments, priming the catheter system may include attaching an IV line to the first arm and delivering saline through the IV line to the catheter system such that the saline exits a distal tip of the catheter. In some embodiments, after the catheter is primed, the IV line may be clamped via a roller clamp or other clamping device on the IV line to occlude the flow of saline in the IV line. In some embodiments, clamping the IV line to occlude flow may displace fluid distally and may result in an increase in system pressure within the catheter system. In some embodiments, the method may also include actuating the vent cap after priming the catheter system. In some embodiments, actuating the vent cap that is coupled to the second arm of the Y-adapter after the priming and clamping steps may relieve the system pressure in the catheter system caused by priming and clamping the IV line. In some embodiments, the method may further include inserting the catheter into a vein of a patient after actuating the vent cap.

In some embodiments, priming the catheter system may include removing all air from the Y-adapter except for air disposed within the second arm of the Y-adapter. In some embodiments, in response to inserting the catheter into the vein of the patient after actuating the vent cap, the air disposed within the second arm of the Y-adapter may exit the catheter system via the vent cap. This is because the vent cap allows air to escape the catheter system as blood enters the catheter system.

In some embodiments, the catheter system may include an introducer needle, which may include a distal notch. In some embodiments, the method of placing the catheter into the vein of the patient may include collecting blood flashback in a space between an outer surface of the introducer needle and an inner surface of the catheter. In some embodiments, venting the second arm of the Y-adapter after priming may facilitate blood flashback, which may indicate to a user that a distal tip of the introducer needle and the distal tip of the catheter are disposed within the vein. In some embodiments, blood flashback may be enhanced compared to blood flashback when the catheter is inserted into the vein after priming but without actuating the vent cap following priming.

In some embodiments, the catheter system may include a first connector coupled to the first arm and/or a second connector coupled to the second arm. In some embodiments, the vent cap may be coupled to the second connector. In some embodiments, the first connector and/or the second connector may include a needleless connector. In some embodiments, the first connector and/or the second connector may include a PRN adapter (from the Latin pro re nata).

Various types of vents caps may be used. In some embodiments, the vent cap may include multiple flexible arms, which may be engaged in a snap fit with a flange of the second connector. In some embodiments, the first arm and/or the second arm may include a luer adapter. In some embodiments, the vent cap may be coupled to the luer adapter of the second arm of the Y-adapter. In some embodiments, the vent cap may be coupled to the second connector, which may include a needleless connector, coupled to the second arm of the Y-adapter. In some embodiments, the vent cap may be coupled to the second connector in a first position that does not access or open a valve of the second connector. In some embodiments, the vent cap may be actuated or moved to a second position that accesses or opens the valve of second connector.

In some embodiments, the catheter system may not be primed prior to inserting the catheter into the vein of the patient. In these embodiments, the method of placing the catheter into the vein of the patient may include actuating the vent cap, and inserting the catheter into the vein of the patient after actuating the vent cap. In these embodiments, blood flashback may be enhanced compared to blood flashback when the catheter is inserted into the vein of the patient without venting the catheter system using the vent cap. In some embodiments, the catheter system may be primed after actuating the vent cap and before inserting the catheter into the vein of the patient. In these embodiments, the catheter system may be fully primed as the actuated vent cap coupled to the second arm of the luer adapter allows the venting of the air in the second arm and the entire catheter system as compared to the method of priming prior to actuating the vent cap.

It is to be understood that both the foregoing general description and the following detailed description are exemplary and explanatory and are not restrictive of the invention, as claimed. It should be understood that the various embodiments are not limited to the arrangements and instrumentality shown in the drawings. It should also be understood that the embodiments may be combined, or that other embodiments may be utilized and that structural changes, unless so claimed, may be made without departing from the scope of the various embodiments of the present invention. The following detailed description is, therefore, not to be taken in a limiting sense.

BRIEF DESCRIPTION OF THE SEVERAL VIEWS OF THE DRAWINGS

Example embodiments will be described and explained with additional specificity and detail through the use of the accompanying drawings in which:

FIG. 8 is a flow chart illustrating another example method of placing a catheter into a vein of a patient, according to some embodiments.

DESCRIPTION OF EMBODIMENTS

Figure 1A:
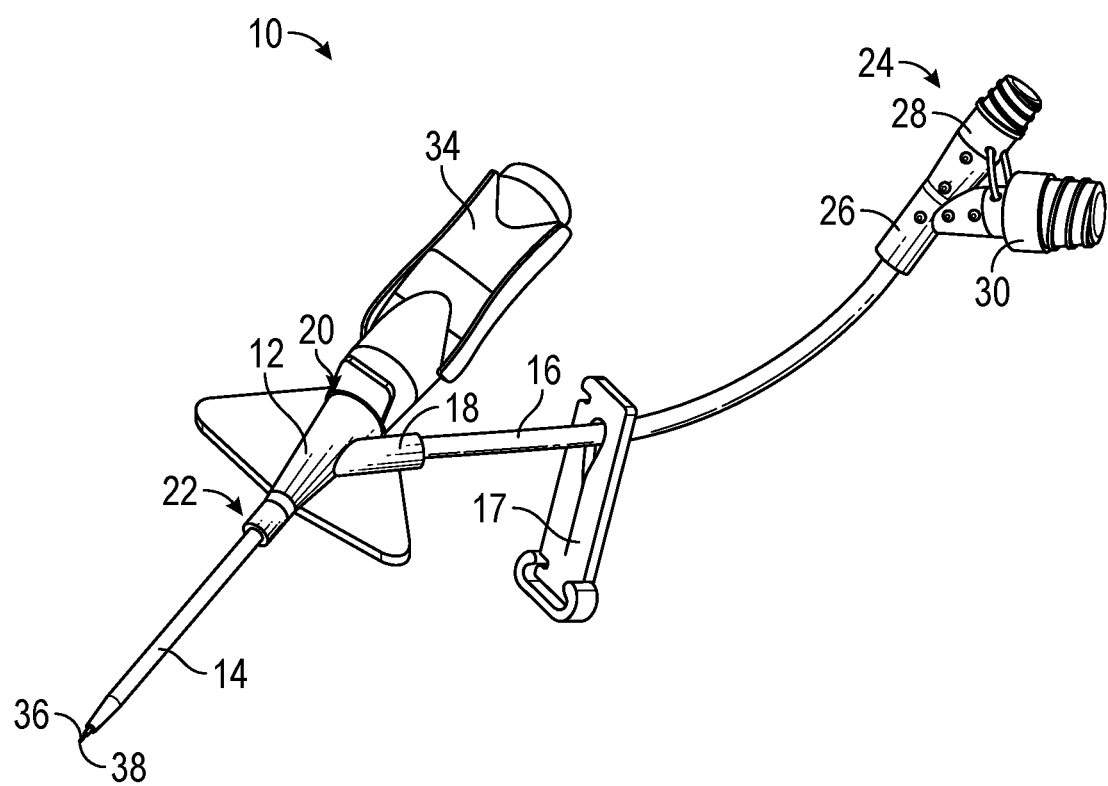
FIG. 1A is an upper perspective view of an example catheter system, according to some embodiments.

The present disclosure relates generally to systems and methods for catheter insertion and blood flashback. Referring now to FIG. 1A, in some embodiments, a catheter system 10 may include a catheter adapter 12, a catheter 14 extending distally from the catheter adapter 12, and an extension tube 16 extending from the catheter adapter 12. In some embodiments, the catheter adapter 12 may include a side port 18. In some embodiments, the extension tube 16 may extend from the side port 18. In some embodiments, the catheter adapter 12 may include a proximal end 20 and a distal end 22. In some embodiments, the extension tube may extend from the proximal end 20 of the catheter adapter 12.

In some embodiments, the catheter system 10 may also include a Y-adapter 24, which may include a distal end 26, a first arm 28, and a second arm 30. In some embodiments, the first arm 28 may correspond to a central arm of the Y-adapter 24, as illustrated in FIG. 1A. In these embodiments, the second arm 30 may correspond to a side arm of the Y-adapter 24, as illustrated in FIG. 1A. Conversely, in some embodiments, the first arm 28 may correspond to the side arm of the Y-adapter 24 and the second arm 30 may correspond to the central arm of the Y-adapter 24.

In some embodiments, the distal end 26 of the Y-adapter 24 may be coupled to the extension tube 16. In some embodiments, the extension tube 16 may include a clamp 17, which may selectively close off the extension tube 16 to prevent blood or another fluid from flowing through the extension tube 16.

In some embodiments, the catheter system 10 may include a needle assembly 32, which may include a needle hub 34 and an introducer needle 36. In some embodiments, the introducer needle 36 may include a distal notch (see, for example distal notch 71 illustrated in FIG. 3).

In some embodiments, the catheter system 10 may include the BD NEXIVA™ Closed IV Catheter System, the BD NEXIVA™ DIFFUSICS™ Closed IV Catheter System, the Becton Dickinson PEGASUS™ Safety Closed IV Catheter System, or another integrated catheter system. In other embodiments, the catheter system 10 may be non-integrated.

Figure 1B:
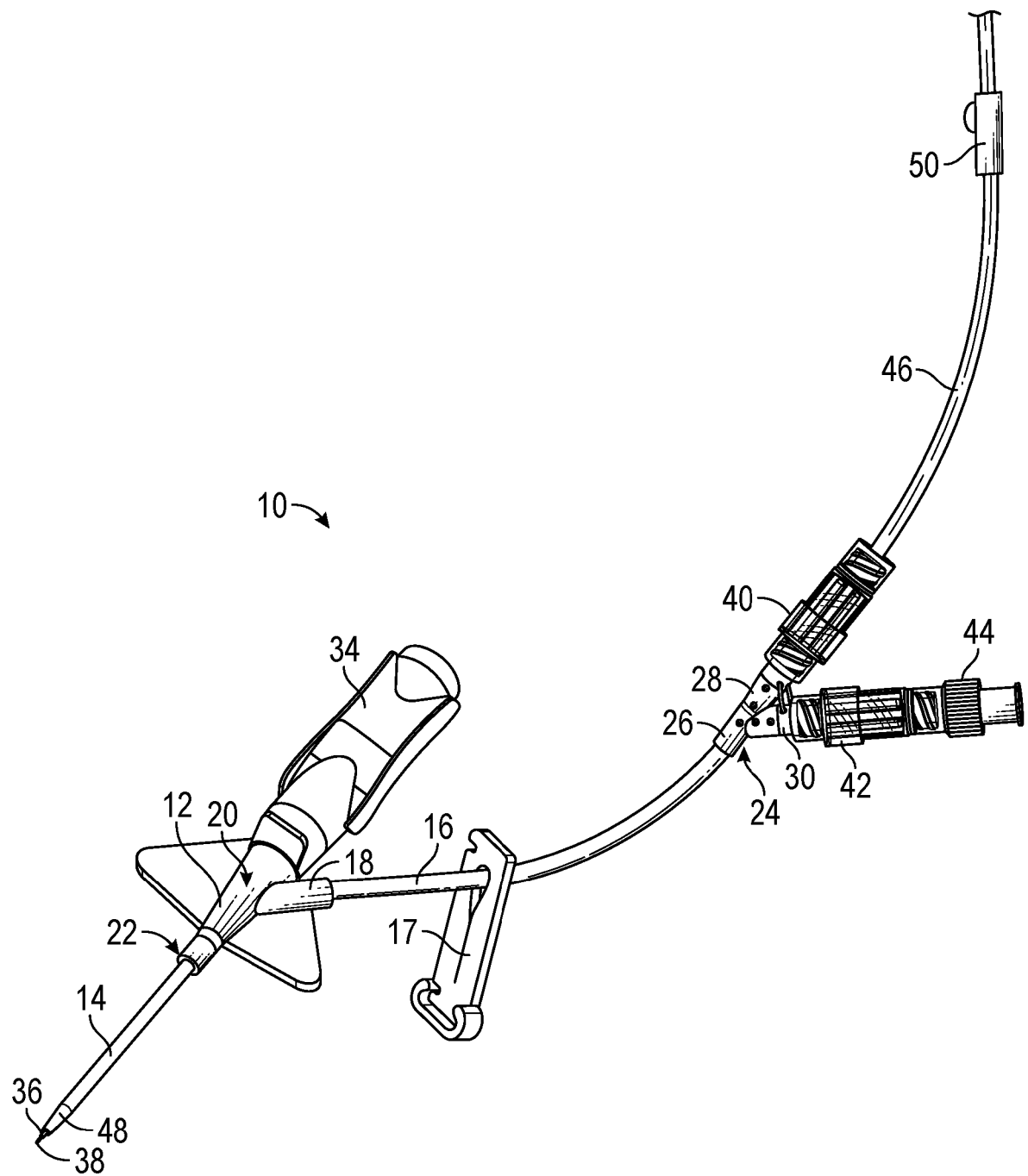
FIG. 1B is an upper perspective view of the catheter system of FIG. 1A having an example first connector and an example second connector and coupled to an example IV line, according to some embodiments.

Referring now to FIG. 1B, in some embodiments, the catheter system 10 may include a first connector 40 coupled to the first arm 28 and/or a second connector 42 coupled to the second arm 30. In some embodiments, the first connector 40 and/or the second connector 42 may include a needleless connector or another suitable type of connector. In some embodiments, the first connector 40 and/or the second connector 42 may include a PRN adapter.

In some embodiments, the catheter system 10 may further include a vent cap 44, which may be coupled to the second arm 30. In some embodiments that include a PRN adapter, a blunt or piercing plastic or metal cannula may be incorporated on the distal end of the vent cap 44 to access and actuate a non-luer connection of the PRN connector. In some embodiments, the vent cap 44 may be directly coupled to the luer adapter of the second arm 30. In other embodiments, the vent cap 44 may be coupled to the second arm 30 via the second connector 42.

In some embodiments, the first arm 28 and/or the second arm 30 may include a luer adapter, such as a slip or thread male or female luer adapter, or another suitable connector. In some embodiments, a proximal end and/or a distal end of the first connector 40 may include a luer adapter, such as a slip or thread male or female luer adapter. In some embodiments, a proximal end and/or a distal end of the second connector 42 may include a luer adapter, such as a slip or thread male or female luer adapter.

In some embodiments, in response to the introducer needle 36 being inserted into the vein of the patient, flashback of blood may flow through a sharp distal tip 38 of the introducer needle 36 and out of the distal notch 71 into a portion of the catheter system 10. For example, the blood flashback may flow through the distal tip 38 and out of the distal notch 71 into a space between an exterior surface of the introducer needle 36 and an interior surface of the catheter 14 (this may be referred to as "primary flashback"). In some embodiments, blood flashback may flow into the extension tube 16 (this may be referred to as "secondary flashback"). Primary and/or secondary blood flashback may confirm that the introducer needle 36 is located within the vein of the patient.

In some markets, priming of a particular catheter system prior to insertion into the patient is common practice. In order to prime the catheter system 10, the user may fill the catheter system 10 with priming solution or another priming fluid to reduce or eliminate air pockets disposed within the particular catheter system. The priming solution may also fill a portion of a lumen of the introducer needle 36 proximate the notch 71, as well as distal to the notch 71, all the way to the distal tip 38 of the introducer needle 36. Thus, when the distal tip 38 of the introducer needle 36 enters the vasculature, blood flashback may be slowed, visually more difficult to see, and may not travel as far into the catheter system due to the presence of saline and diffusion. In some embodiments, the present disclosure relates to a method of improving blood flashback after the catheter system 10 is primed.

In some embodiments, priming the catheter system 10 may include attaching an IV line 46 or other suitable priming device to the first arm 28 and delivering priming solution through the IV line 46 to the catheter system 10 such that the priming solution exits a distal tip 48 of the catheter 14 and/or the distal tip 38 of the introducer needle 36, and then clamping the IV line 46 via a roller clamp 50 on the IV line 46. In some embodiments, the priming solution may include saline or another suitable solution. FIG. 1B illustrates the roller clamp 50 in an open position, in which the priming solution is able to flow into the catheter system 10 for priming. In some embodiments, priming the catheter system 10 may include removing all air from the Y-adapter 24 except for air disposed within the second arm 30 of the Y-adapter 24. The air within the second arm 30 may be unable to escape due to lack of venting. In some embodiments, after priming the catheter system 10, there may be air remaining in the catheter system 10 within the second arm 30 and/or the second connector 42.

Figure 1C:
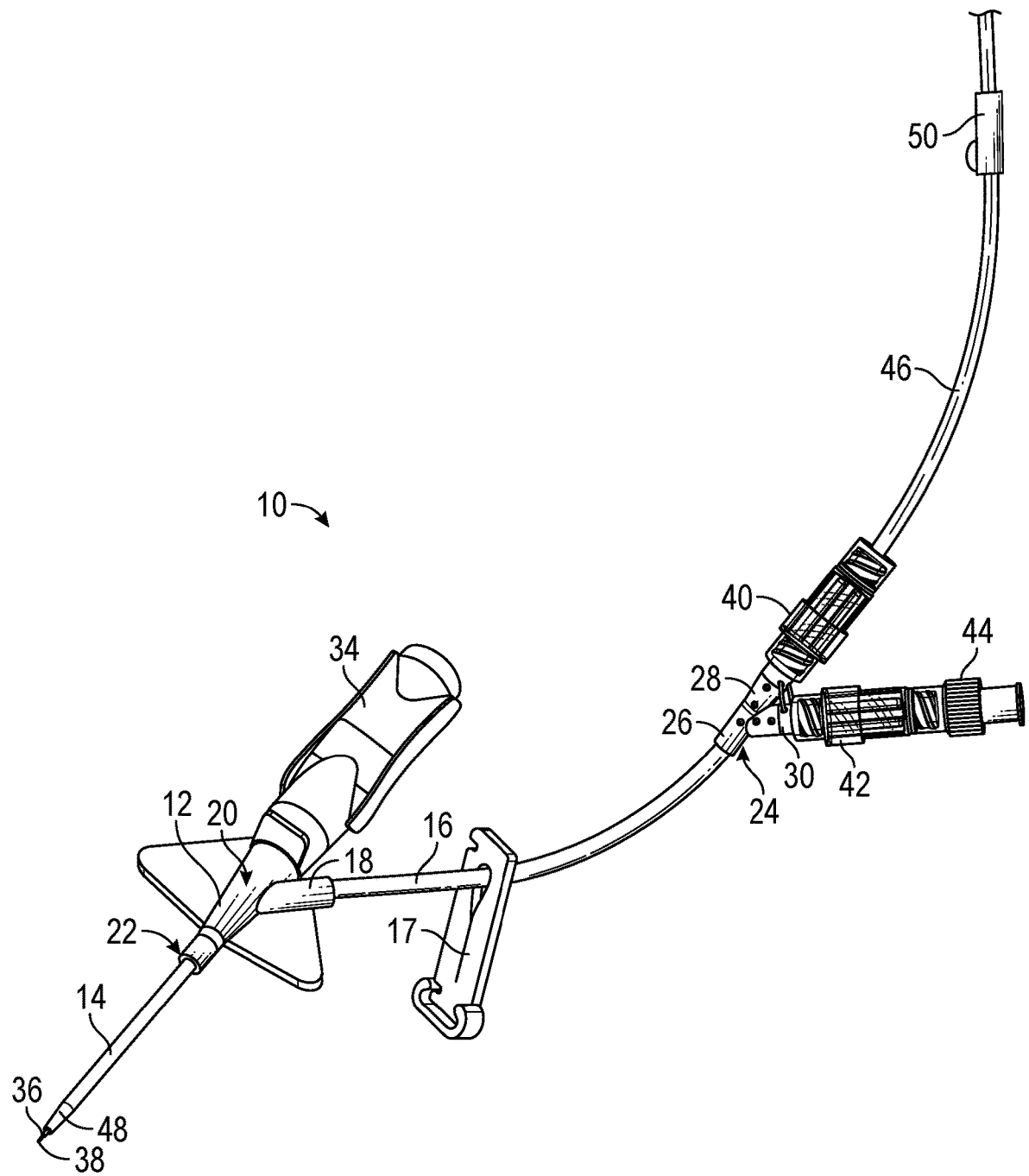
FIG. 1C is an upper perspective view of the catheter system of FIG. 1B, illustrating an example roller clamp in a closed position and an example vent cap in an unactuated position, according to some embodiments.

Referring now to FIG. 1C, the roller clamp 50 is illustrated in a closed position, according to some embodiments. In some embodiments, when the roller clamp 50 is moved to the closed position, fluid may be prevented from flowing through the IV line 46. In some embodiments, in response to movement of the roller clamp 50 to the closed position after priming and without actuating the vent cap 44, fluid displacement may occur within the IV line 46, which may create a residual pressure within the catheter system 10 that leads to a continued slow drip of the priming solution from the distal tip 38 until the residual pressure is relieved. The dripping of priming solution may occur for up to 30 seconds or more depending on a gauge size of the catheter 14 or other factors. In some embodiments, during the time spent waiting for relief of the residual pressure, ongoing softening of the catheter 14 may occur, which may lead to less favorable insertion conditions. In some instances, if the user does not wait until the dripping of priming solution has stopped, vein confirmation via blood flashback may be limited.

In some embodiments, the air trapped within the second arm 30 and/or the second connector 42 may be taken advantage of in order to relieve the residual pressure and/or improve the blood flashback after priming. In further detail, in some embodiments, the method may also include actuating the vent cap 44 after priming the catheter system 10. An actuated vent cap 44 may provide venting to the catheter system 10, while an unactuated vent cap 44 may not. In some embodiments, the method may further include inserting the catheter 14 into the vein of a patient after actuating the vent cap 44.

Actuating the vent cap 44 after priming may relieve the residual pressure and allow the user to insert the catheter into the vein of the patient and visualize blood flashback without waiting the approximately 30 seconds or more for the dripping of the priming solution to slow or stop. In further detail, in some embodiments, in response to inserting the catheter 14 into the vein of the patient after actuating the vent cap 44, the air disposed within the second arm 30 of the Y-adapter 24 may exit the catheter system 10 via the vent cap 44. In some embodiments, the air may escape the catheter system 10 via the vent plug 44 to relieve the residual pressure and to allow the venous pressure to push the priming solution proximally within the second arm 30 and/or the second connector 42 as the blood flashback enters the catheter system 10.

In some embodiments, venting the second arm 30 of the Y-adapter 24 after priming may facilitate the blood flashback, which may enter the catheter 14, the catheter adapter 12, and a portion of the extension tubing to indicate to a user that the distal tip 38 of the introducer needle 36 and the distal tip 48 of the catheter 14 are disposed within the vein. In some embodiments, blood flashback may be enhanced compared to blood flashback when the catheter 14 is inserted into the vein after priming but without actuating the vent cap 44 following priming. In some embodiments, priming the catheter system 10 without actuating the vent cap 44 following priming may slow blood flashback in response to insertion of the catheter 14 into the vein of the patient due to the residual pressure resulting from closing the roller clamp and slower diffusion of blood into the catheter system.

Figure 1D:
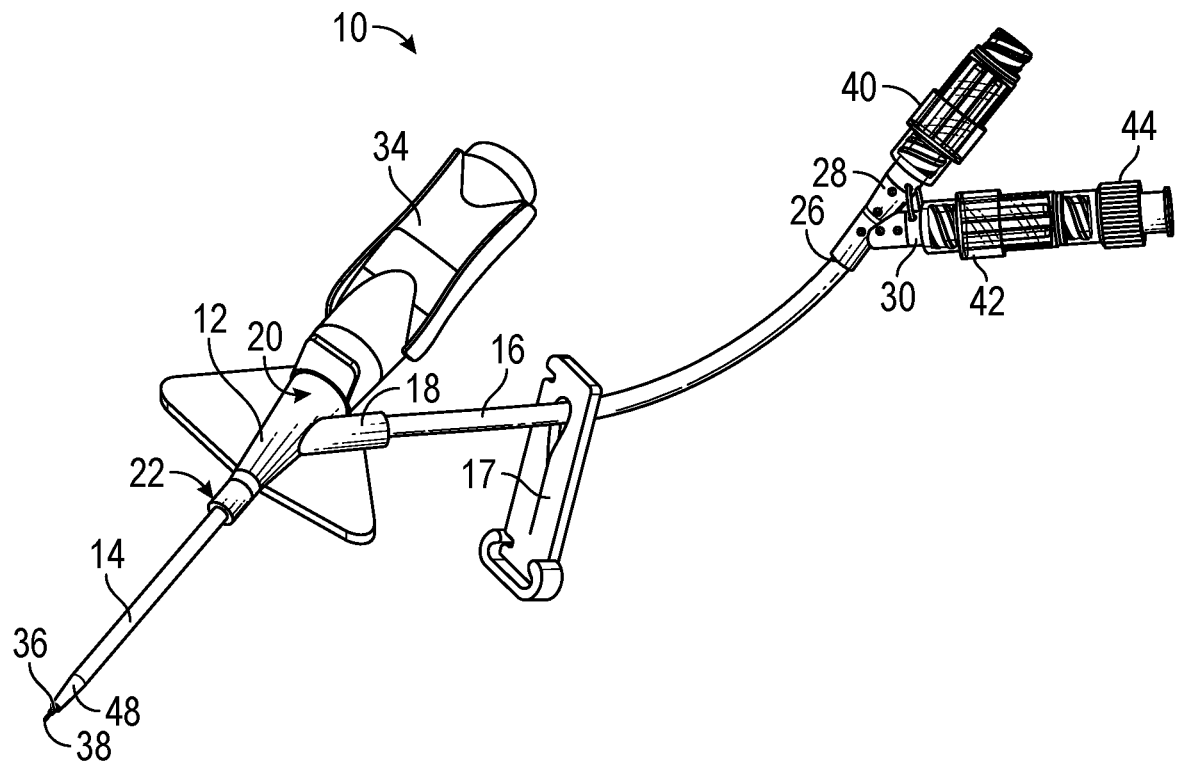
FIG. 1D is an upper perspective view of the catheter system of FIG. 1B, illustrating the vent cap in an actuated position, according to some embodiments.

Referring now to FIG. 1D, in some embodiments, the IV line 46 may be uncoupled from the catheter system 10 after the catheter system 10 is primed and/or the vent cap 44 is actuated. In some embodiments, when collection of one or more blood samples is desired using the catheter system 10, the catheter system 10 may not be primed or connected to the IV line 46. In these and other embodiments, the vent cap 44 may be actuated to allow blood to fill the unprimed catheter system 10 by venting the second arm 30 to which the vent cap 44 may be attached. In some embodiments, after the catheter 14 is inserted into the vein and blood fills the extension tubing, the vent cap 44 may be removed, and a blood collection device (such as, for example, a vacuum tube holder, syringe, or another device) may be attached to the first arm 28 or second arm 30 to collect the blood samples via the blood collection device. In these and other embodiments, without priming, pulling a discard sample to remove saline from the extension tube 16 and/or Y-adapter 24 may not be needed.

In some embodiments, the blood collection device may be connected to the first arm 28 prior to insertion of the catheter 14 into the patient and after the vent cap 44 is actuated. In some embodiments, the blood collection device may be connected to the first arm 28 prior to insertion of the catheter 14 into the patient and before the vent cap 44 actuated. In some embodiments, when the blood fills the extension tubing, the blood collection device may then be actuated to collect the blood sample without a need for the discard sample.

Figure 1E:
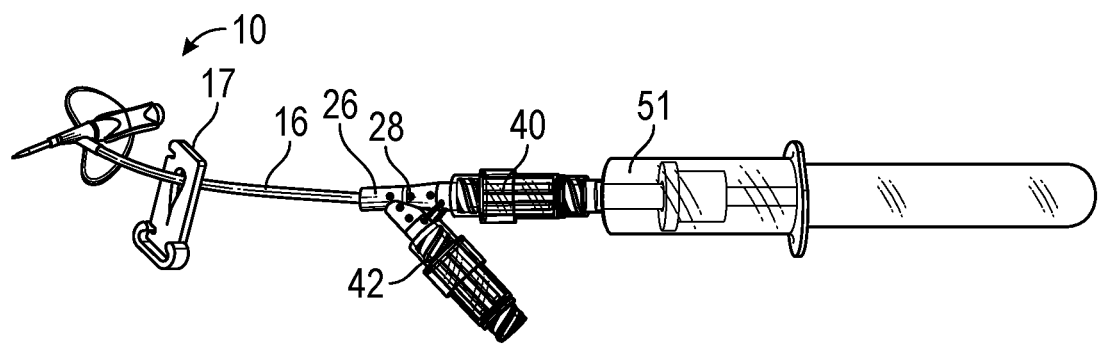
FIG. 1E is an upper perspective view of the catheter system of FIG. 1B coupled with an example blood collection device, according to some embodiments.

Referring now to FIG. 1E, in some embodiments, a blood collection device 51 may be coupled to the Y-adapter 24. In some embodiments, the blood collection device 51 may be coupled to the Y-adapter after priming of the catheter system 10 or without priming the catheter system 10. In some embodiments, the blood collection device 51 may be coupled to the first arm 28 of the Y-adapter.

In some embodiments, the blood collection device 51 may include any suitable type of blood collection device. In some embodiments, the blood collection device 51 may include a reservoir. In some embodiments, the blood collection device 51 may include a vacuum tube, test tube, or syringe. In some embodiments, the blood collection device 51 may include an adapter, which may be configured to hold a test tube or syringe.

Figure 2A:
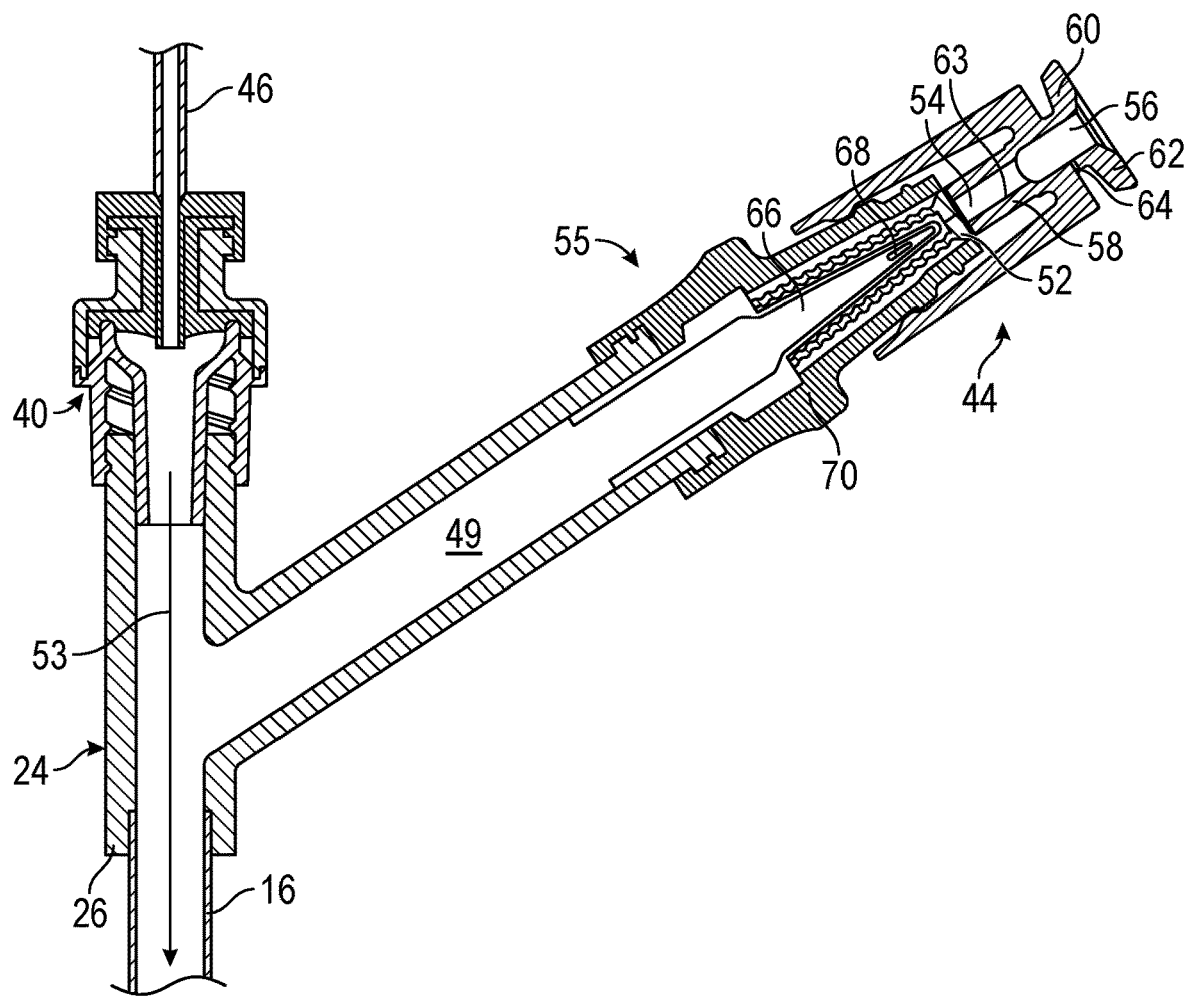
FIG. 2A is a cross-sectional view of the catheter system of FIG. 1B coupled with another example vent cap, illustrating an example needleless connector, according to some embodiments.
Figure 2B:
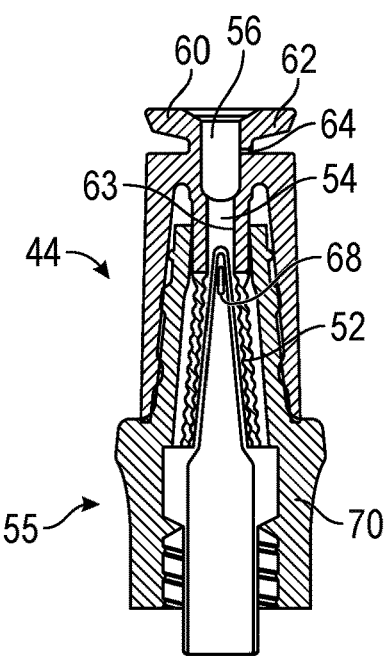
FIG. 2B is a cross-sectional view of the vent cap of FIG. 2A in an actuated position, according to some embodiments.

In some embodiments, various types of vent caps or similar venting devices may be used with the catheter system 10. Referring now to FIGS. 2A-2B, another example vent cap 44 is illustrated, according to some embodiments. FIG. 2A also illustrates, according to some embodiments, an unprimed volume 49 and a priming solution pathway 53, which may include an air pocket.

In some embodiments, the vent cap 44 may be assembled to the second connector 42, which may include a needleless connector, and movable or shiftable between a first, storage or unactuated position (illustrated, for example, in FIG. 2A), in which a compression seal 52 of the needleless connector is in an uncompressed state, thereby inhibiting fluid from passing through a vent path 54, and a second, actively depressed position (illustrated, for example, in FIG. 2B), in which the compression seal 52 of the needleless connector is in a compressed state, thereby permitting fluid to pass through vent path 54.

In some embodiments, an air permeable barrier 56 may be positioned within a portion of the vent path 54. In some embodiments, the air permeable barrier 56 may be comprised of an air permeable matrix that enables air or gas to vent as blood fills the vent path 54, but inhibits the priming fluid, saline, blood or other fluid from passing entirely through the vent path 54. In some embodiments, the vent cap 44 can be constructed of a transparent or translucent material. In some embodiments, during the venting of air, blood can fill a portion of the vent path 54, thereby providing a visual confirmation to the user that the catheter 14 has been inserted into the vein of the patient. Such visual confirmation can be referred to as secondary or tertiary blood flashback.

In some embodiments, a nose 58 may terminate in a push plate 60. In some embodiments, the push plate 60 may include a flange 62 configured to provide a surface area for a user to push on as the vent cap 44 is manually shifted between the first, storage position and the second, actively depressed position. In one embodiment, a portion of the vent path wall 63 may further define an eyelet 64. In some embodiments, the eyelet 64 may be configured to provide a fluid path for venting air between the vent path 54 and an exterior of the vent path wall 63. In particular, in some embodiments, the eyelet 64 may provide a path for escaping air in the event that the user seals the end of the vent path 54 with their finger as the vent cap 44 is shifted to the second, actively depressed position. In one embodiment, portions of the vent cap 44 may include a mechanism configured to provide an audible click and/or tactile feedback when the vent cap 44 has been shifted to the second, actively depressed position.

In some embodiments, various types of first connectors 40 and/or second connectors 42 may be used in the system 10. In some embodiments, various types of needleless connectors may be used as the first connector 40 and/or the second connector 42. Some non-limiting examples of needleless connectors are described in U.S. Pat. No. 8,066,670, filed Nov. 5, 2007, entitled "VASCULAR ACCESS DEVICE SEPTUM VENTING," which is hereby incorporated by reference. Further, in some embodiments, various types of PRN adapters may be used as the first connector 40 and/or the second connector 42.

In FIG. 2A, the second connector 42 includes an example needleless connector, according to some embodiments. In some embodiments, the needleless connector may include one or more of the following: a conical internal conduit 66 with one or more fluid path windows 68, a flexible compression seal 52 capable of selectively covering the internal conduit 66, and a housing 70 substantially surrounding the internal conduit 66 and the compression seal 52. In some embodiments, the exterior of the housing 70 may include a substantially smooth surface, in which crevices are minimized to promote ease in having a surface that is readily swabbed or cleaned to prevent the growth and/or presence of microbes. In some embodiments, an interior of the housing 70 may be configured to promote a more even flow of fluid to improve flushability of the needleless connector. In one embodiment, the interior of the housing 70 may be shaped to reduce the occurrence of dead spaces or pockets, thereby reducing the areas where microbial growth is likely to occur.

In some embodiments, the needleless connector and/or PRN adapter may prevent the escape of bodily fluid and/or guard against contamination of the fluid path of the catheter system 10. In some embodiments, in a closed or sealed position, the compression seal 52 may extend over the fluid path windows 68 of the internal conduit 66, thereby creating a fluid seal to prevent fluid from escaping from the extension tube 16, as illustrated, for example, in FIG. 2A. Conversely, in some embodiments, as illustrated in FIG. 2B, when the vent cap 44 is actuated and inserted into the housing 70, the compression seal 52 may be shifted to an open position, thereby exposing the fluid path windows 68 to the fluid path of the vent cap 44.

In some embodiments, the first connector 40 and/or the second connector 42 may enable the catheter system 10 to act as a closed system when not connected to IV line 46 or another medical device. In some embodiments, a particular needleless connector or a particular PRN adapter, in combination with a particular vent cap, may prevent blood from escaping from the catheter system 10, thus maintaining the closed system.

Figure 3:
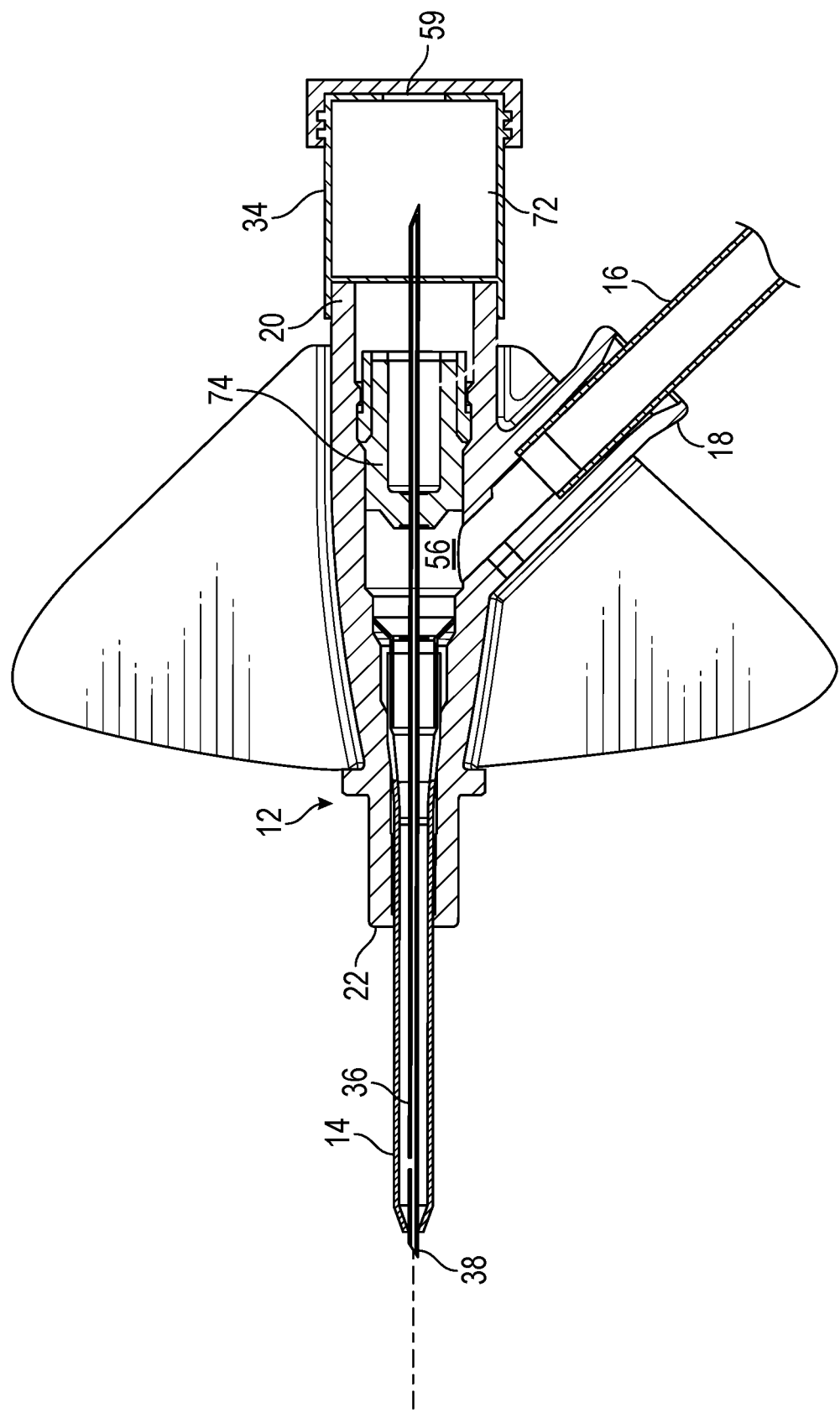
FIG. 3 is a cross-sectional view of an example catheter adapter and example needle hub, according to some embodiments.

Referring now to FIG. 3, in some embodiments, the catheter system 10 may include flashback chamber 72, which may be fluidly connected to a proximal end of the introducer needle 36. In some embodiments, the introducer needle 36 may extend through a septum 74 when the introducer needle 36 is in an insertion position for insertion into the patient, as illustrated in FIG. 3, for example. In some embodiments, the flashback chamber 72 may include a venting feature which may be unactuated during priming of the catheter system 10 and/or actuated after priming of the catheter system 10 prior to insertion of the catheter 14 into the patient. In some embodiments, the flashback chamber 72 may be used to relieve the residual pressure resulting from the priming of the catheter system 10 and/or clamping the IV line 46. In further detail, in some embodiments, priming the catheter system 10 may leave an air pocket within the flashback chamber 72. In some embodiments, venting the flashback chamber 72 after the catheter system 10 is primed may remove the air pocket, reduce the residual pressure, and allow blood to flow into the flashback chamber 72 when the catheter system 10 is inserted into the vein.

In some embodiments, the venting feature may include a vent cap, which may be movable between an actuated and unactuated position. The vent cap may include any features of the vent caps described in the present disclosure, according to some embodiments. In some embodiments, the venting feature may include an air vent 59, which may include a hydrophobic membrane or other filter that allows air but not fluid to pass. In some embodiments, the air vent may be actuated by removing an air-tight cap covering the air vent. In some embodiments, the air vent may be unactuated by covering the air vent with the cap, as illustrated, for example, in FIG. 3.

In some embodiments, the flashback chamber 72 having the venting feature may reduce or eliminate a "false positive" scenario in which blood may continue to fill a particular flashback chamber even when an introducer needle transfixes the vein. In some embodiments, the flashback chamber 72 may vary in terms of its size and configuration. In some embodiments, the flashback chamber 72 may include one or more features disclosed in U.S. patent application Ser. No. 15/286,188, which is hereby incorporated by reference in its entirety.

Figure 4:
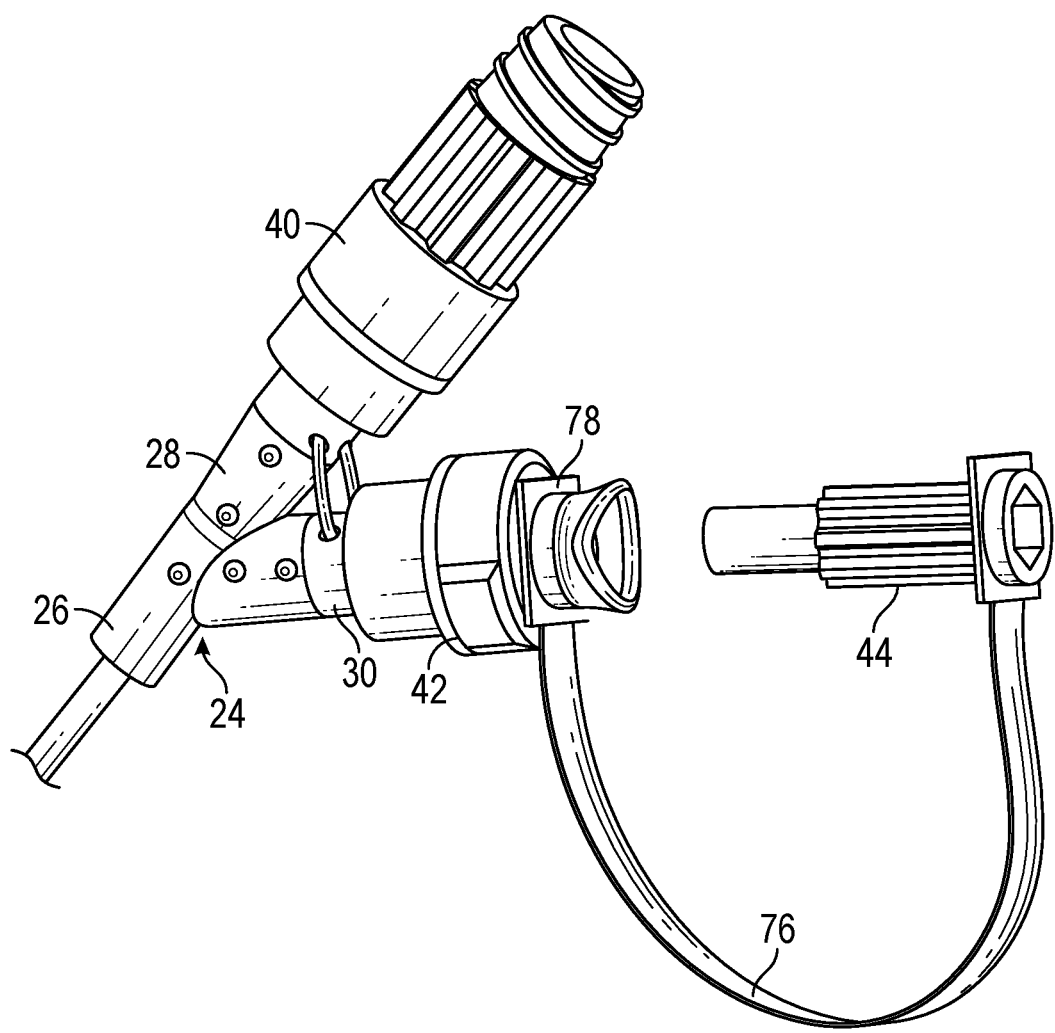
FIG. 4 is an upper perspective view of another example vent cap, according to some embodiments.

Referring now to FIG. 4, in some embodiments, the vent cap 44 may be coupled to the Y-adapter 24 and/or the second connector 42 via a tether 76. In some embodiments, the second arm 30 and/or the second connector 42 may be inserted into an aperture or hole of an attachment element 78 disposed at a distal end of the tether 76. In some embodiments, the catheter system 10, including the vent cap 44, may be packaged together in a kit.

Figure 5A:
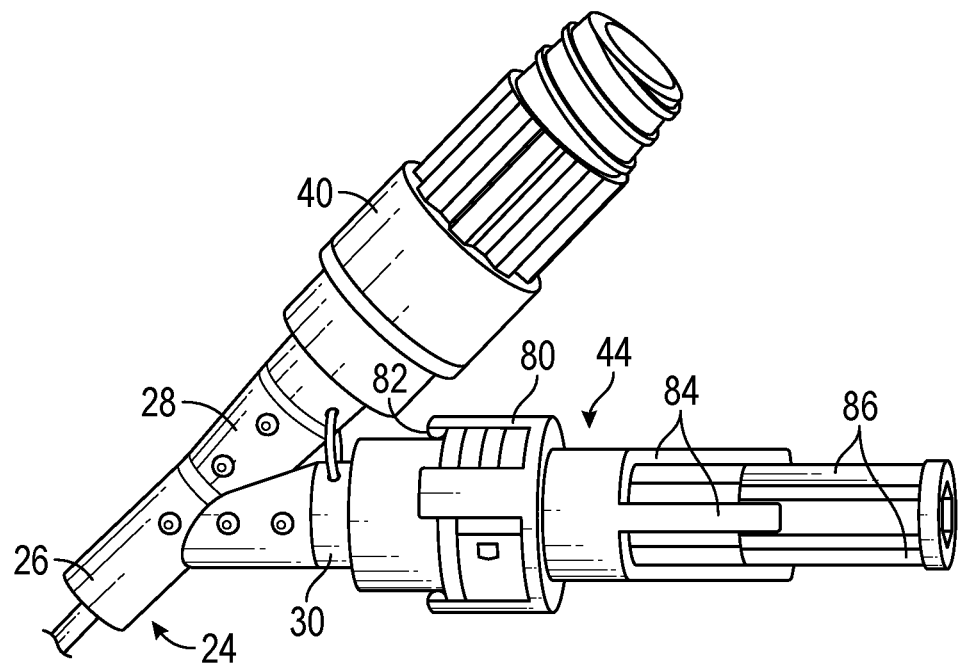
FIG. 5A is an upper perspective view of another example vent cap, according to some embodiments.
Figure 5B:
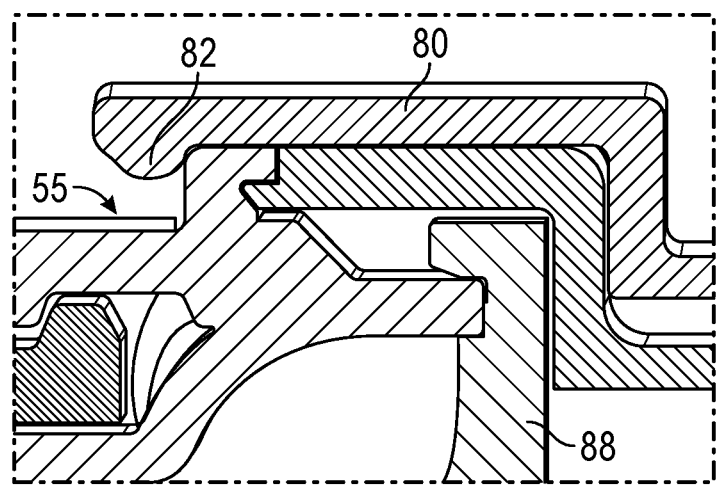
FIG. 5B is a cross-sectional view of a portion of the vent cap of FIG. 5A, according to some embodiments.
Figure 5C:
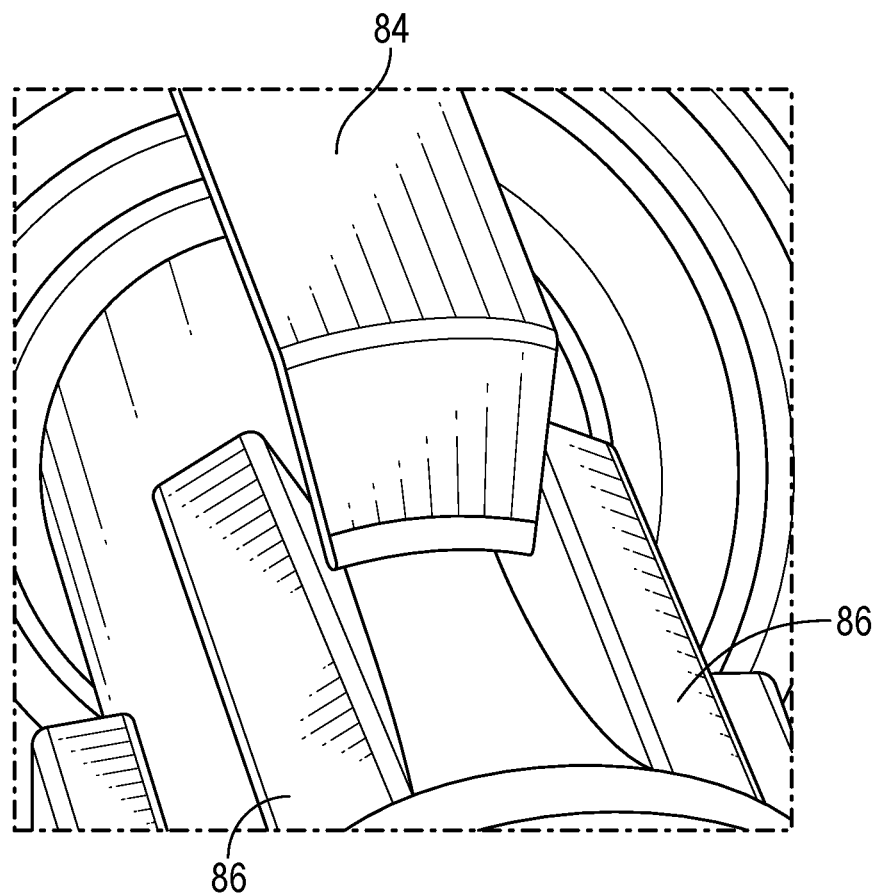
FIG. 5C is an upper perspective view of another portion of the vent cap of FIG. 5A, according to some embodiments.

Referring now to FIG. 5A-5C, in some embodiments, the vent cap 44 may include multiple engagement arms 80, which may be configured to grip a portion of the Y-adapter 24 or the second connector 42. In some embodiments, the engagement arms 80 may be constructed of a resilient material, such that the engagement arms 80 tend to regain their original shape after temporary deformation. In some embodiments, the engagement arms 80 may be biased outwardly to snap onto the Y-adapter 24 or the second connector 42. In some embodiments, ends of the engagement arms 80 may include flanges 82, which may abut a flange of the Y-adapter 24 or the second connector 42 and prevent the vent cap 44 from moving proximally.

In some embodiments, the vent cap 44 may include one or more other arms 84, which may be disposed in one or more slots 86 of a movable piece of the vent cap 44. In some embodiments, the arms 82 disposed within the slot may support the vent cap 44 as it moves between an actuated or distal position and an unactuated or proximal position.

Figure 5D:
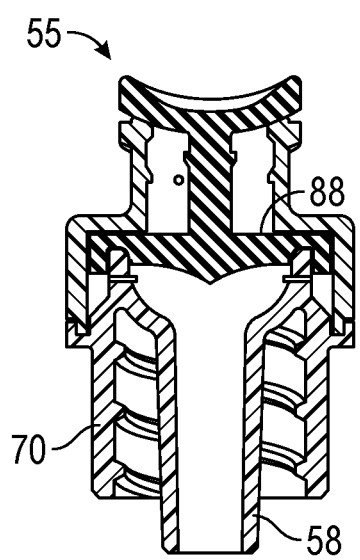
FIG. 5D is a cross-sectional view of an example needleless connector, according to some embodiments.

FIG. 5D illustrates another example needleless connector, according to some embodiments. The second connector illustrated in FIGS. 5A-5B may correspond to the needleless connector of FIG. 5D. In some embodiments, the septum 88 may prevent blood from exiting the catheter system 10. The needleless connector of FIG. 5D may be described in further detail in U.S. Pat. No. 8,066,670, filed Nov. 5, 2007, entitled "VASCULAR ACCESS DEVICE SEPTUM VENTING," which is hereby incorporated by reference.

Figure 6:
FIG. 6 is a flow chart illustrating an example method of placing a catheter into a vein of a patient, according to some embodiments.

Referring now to FIG. 6, a flow diagram of an example method 100 of placing a catheter into a vein of a patient is illustrated, according to some embodiments. The method may begin at block 102. In block 102, a catheter system may be primed. In some embodiments, priming the catheter system clamping of an IV line, such as, for example, the IV line 46, discussed with respect to one or more of the previous Figures. In some embodiments, the catheter system may include or correspond to the catheter system 10 as described with respect to one or more of FIGS. 1-5. In some embodiments, block 102 may be followed by block 104.

In block 104, a vent cap of the catheter system may be actuated. In some embodiments, the vent cap may include or correspond to the vent cap 44 as described with respect to one or more of FIGS. 1-5. In some embodiments, block 104 may be followed by block 106.

In block 106, a catheter of the catheter system may be inserted into the vein of the patient after the vent cap is actuated. The method of FIG. 6 may further be described with respect to one or more of FIGS. 1-5. Various elements used in the method of FIG. 6 may also be further described with respect to one or more of FIGS. 1-5. Although illustrated as discrete blocks, various blocks of method 100 may be divided into additional blocks, combined into fewer blocks, or eliminated, depending on the desired implementation.

Figure 7:
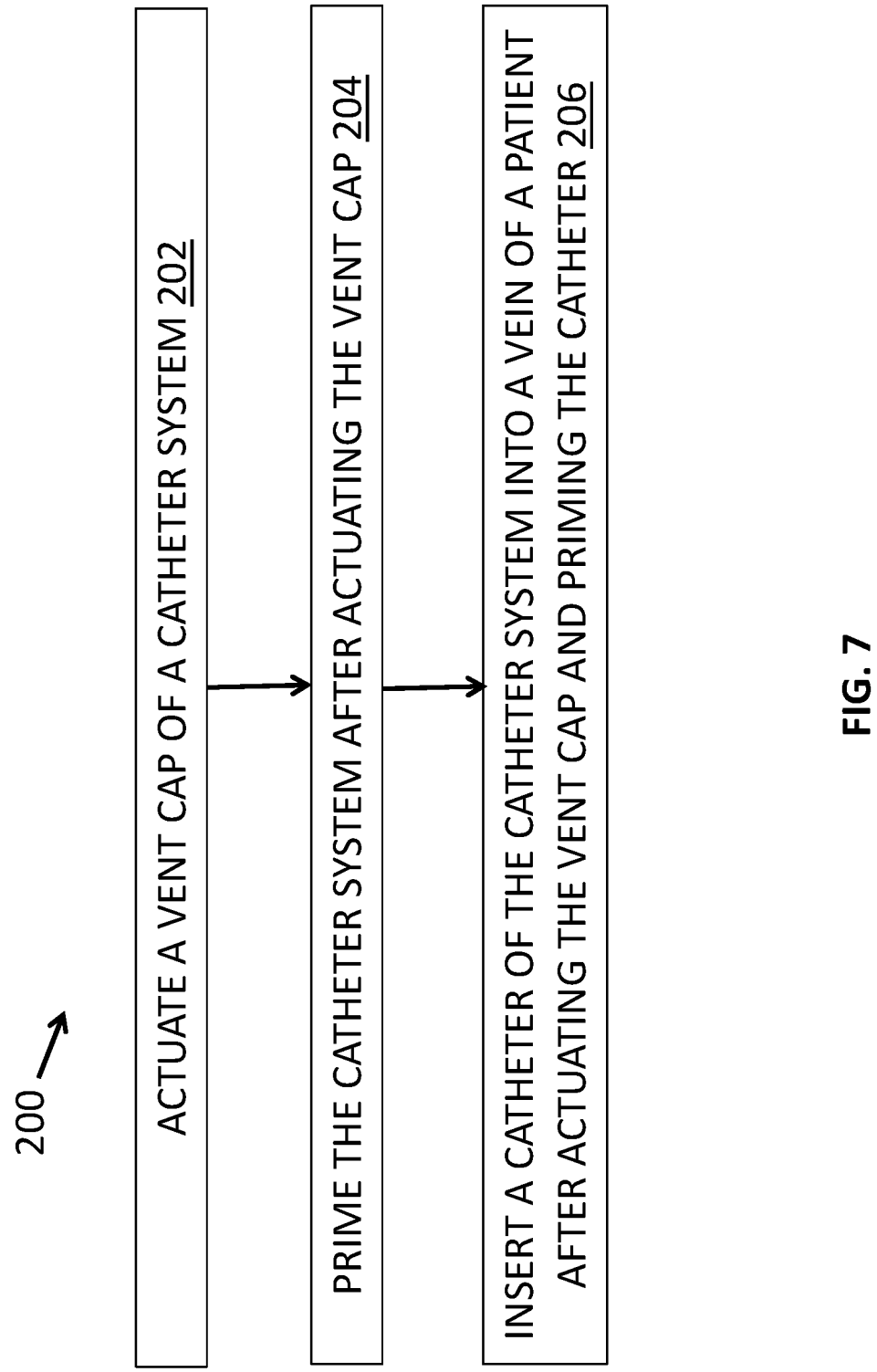
FIG. 7 is a flow chart illustrating another example method of placing a catheter into a vein of a patient, according to some embodiments.

Referring now to FIG. 7, a flow diagram of another example method 200 of placing a catheter into a vein of a patient is illustrated, according to some embodiments. The method may begin at block 202. In block 202, a vent cap of a catheter system may be actuated. In some embodiments, the catheter system may include or correspond to the catheter system 10 as described with respect to one or more of FIGS. 1-5. In some embodiments, the vent cap may include or correspond to the vent cap 44 as described with respect to one or more of FIGS. 1-5. Block 202 may be followed by block 204.

In block 204, the catheter system may be primed after actuating the vent cap. Block 204 may be followed by block 206. At block 206, a catheter of the catheter system may be inserted into the vein of the patient after actuating the vent cap and priming the catheter. In further detail, in some embodiments, the catheter system may be primed after actuating the vent cap and before inserting the catheter into the vein of the patient, which may provide a fully vented and therefore fully primed catheter system that prevents residual air from being delivered to the patient.

The method of FIG. 6 may provide enhanced flashback compared to the method of FIG. 7. However, the method of FIG. 7 may provide enhanced flashback compared to a method that does not include actuating the vent plug at all. The method of FIG. 7 may further be described with respect to one or more of FIGS. 1-5. Various elements used in the method of FIG. 7 may also be further described with respect to one or more of FIGS. 1-5. Although illustrated as discrete blocks, various blocks of method 100 may be divided into additional blocks, combined into fewer blocks, or eliminated, depending on the desired implementation.

Referring now to FIG. 8, a flow diagram of another example method 300 of placing a catheter into a vein of a patient, according to some embodiments. The method may begin at block 302. In block 302, a vent cap of a catheter system may be actuated. Block 302 may be followed by block 304.

In block 304, a catheter of the catheter system may be inserted into the vein of the patient after actuating the vent cap. In some embodiments, the catheter system may not be primed prior to insertion of the catheter into the vein. Block 304 may be followed by block 306.

At block 306, a blood sample may be collected after the catheter is inserted into the vein. In further detail, the blood sample may be taken via a blood collection device coupled to the catheter system. In some embodiments, the blood sample may be collected without taking a discard sample.

The method of FIG. 8 may further be described with respect to one or more of FIGS. 1-5. Various elements used in the method of FIG. 8 may also be further described with respect to one or more of FIGS. 1-5. Although illustrated as discrete blocks, various blocks of method 100 may be divided into additional blocks, combined into fewer blocks, or eliminated, depending on the desired implementation. For example, block 306 may be eliminated.

It is understood that in some embodiments, the catheter system may not be primed prior to inserting the catheter into the vein of the patient. In these embodiments, the method of placing the catheter into the vein of the patient may include actuating the vent cap, and inserting the catheter into the vein of the patient after actuating the vent cap. In these embodiments, blood flashback may be enhanced compared to blood flashback when the catheter is inserted into the vein of the patient without venting the catheter system using the vent cap.

All examples and conditional language recited herein are intended for pedagogical objects to aid the reader in understanding the invention and the concepts contributed by the inventor to furthering the art, and are to be construed as being without limitation to such specifically recited examples and conditions. Although embodiments of the present inventions have been described in detail, it should be understood that the various changes, substitutions, and alterations could be made hereto without departing from the spirit and scope of the invention.

The invention claimed is:

1. A method of placing a catheter into a vein of a patient, comprising:
    actuating a vent cap of a catheter system, wherein the catheter system comprises:
        a catheter adapter;
        a catheter extending distally from the catheter adapter;
        an extension tube extending from the catheter adapter;
        a Y-adapter having a distal end, a first arm, and a second arm, wherein the distal end of the Y-adapter is coupled to the extension tube; and
        a vent cap coupled to the second arm;
    inserting the catheter into a vein of a patient after actuating the vent cap; and
    priming the catheter system after actuating the vent cap and before inserting the catheter into the vein of the patient, wherein priming the catheter system comprises:
        attaching an IV line to the first arm and delivering saline through the IV line to the catheter system such that the saline exits a distal tip of the catheter and removes air in the second arm; and
        clamping the IV line via a roller clamp on the IV line, wherein the vent cap is actuated during priming.

2. A method of placing a catheter into a vein of a patient, comprising:
    actuating a vent cap of a catheter system, wherein the catheter system comprises:
        a catheter adapter;
        a catheter extending distally from the catheter adapter;
        an extension tube extending from the catheter adapter;
        a Y-adapter having a distal end, a first arm, and a second arm, wherein the distal end of the Y-adapter is coupled to the extension tube; and
        a vent cap coupled to the second arm; and
    inserting the catheter into a vein of a patient after actuating the vent cap, wherein the catheter system is not primed prior to inserting the catheter into the vein of the patient.

3. A method of placing a catheter into a vein of a patient, comprising:
    actuating a vent cap of a catheter system, wherein the catheter system comprises:
        a catheter adapter;
        a catheter extending distally from the catheter adapter;
        an extension tube extending from the catheter adapter;
        a Y-adapter having a distal end, a first arm, and a second arm, wherein the distal end of the Y-adapter is coupled to the extension tube; and
        a vent cap coupled to the second arm;
    inserting the catheter into a vein of a patient after actuating the vent cap; and
    coupling a blood collection device to the first arm before inserting the catheter into the vein of the patient.

4. A method of placing a catheter into a vein of a patient, comprising:
    actuating a vent cap of a catheter system, wherein the catheter system comprises:
        a catheter adapter;
        a catheter extending distally from the catheter adapter;
        an extension tube extending from the catheter adapter;
        a Y-adapter having a distal end, a first arm, and a second arm, wherein the distal end of the Y-adapter is coupled to the extension tube; and
        a vent cap coupled to the second arm;

inserting the catheter into a vein of a patient after actuating the vent cap;
removing the vent cap from the second arm after inserting the catheter into the vein of the patient; and
coupling a blood collection device to the first arm or the second arm.

* * * * *